US007010954B2

(12) United States Patent
Siess et al.

(10) Patent No.: US 7,010,954 B2
(45) Date of Patent: Mar. 14, 2006

(54) METHOD FOR CALIBRATING A PRESSURE SENSOR OR A FLOW SENSOR AT A ROTARY PUMP

(75) Inventors: Thorsten Siess, Wuerselen (DE); Christoph Nix, Stolberg (DE); Stefan Boensch, Aachen (DE)

(73) Assignee: Impella CardioSystems AG, (DE)

( * ) Notice: Subject to any disclaimer, the term of this patent is extended or adjusted under 35 U.S.C. 154(b) by 91 days.

(21) Appl. No.: 10/432,298

(22) PCT Filed: Nov. 16, 2001

(86) PCT No.: PCT/EP01/13266

§ 371 (c)(1),
(2), (4) Date: May 21, 2003

(87) PCT Pub. No.: WO02/45775

PCT Pub. Date: Jun. 13, 2002

(65) Prior Publication Data

US 2004/0022640 A1    Feb. 5, 2004

(30) Foreign Application Priority Data

Dec. 5, 2000  (DE)  .............................. 100 60 275

(51) Int. Cl.
    *G01L 27/00*  (2006.01)
(52) U.S. Cl. ..................... 73/1.59; 73/1.61; 73/1.63

(58) Field of Classification Search ........ 73/1.59–1.64, 73/1.67, 1.69
See application file for complete search history.

(56) References Cited

U.S. PATENT DOCUMENTS

| 4,598,579 | A  | * | 7/1986  | Cummings et al. .......... 73/1.63 |
| 5,437,284 | A  | * | 8/1995  | Trimble ..................... 73/1.59 |
| 6,159,160 | A  | * | 12/2000 | Hsei et al. .................. 600/560 |
| 6,234,759 | B1 | * | 5/2001  | Hennel et al. ............. 417/44.1 |
| 6,623,420 | B1 | * | 9/2003  | Reich et al. ................. 600/17 |
| 2003/0139643 | A1 | * | 7/2003 | Smith et al. ................. 600/16 |
| 2004/0106874 | A1 | * | 6/2004 | Eigler et al. ............... 600/486 |

FOREIGN PATENT DOCUMENTS

| WO | WO 97/49439 | 12/1997 |
| WO | WO 98/43688 | 10/1998 |

* cited by examiner

*Primary Examiner*—Hezron Williams
*Assistant Examiner*—Nashmiya Fayyaz
(74) *Attorney, Agent, or Firm*—Fulwider Patton LLP

(57) ABSTRACT

An intracardiac rotary pump (10) is provided with a pressure differential sensor (18) for supporting the pumping heart. The pressure differential sensor measures the pressure differential between aorta (AO) and left ventricle (LV). This pressure differential must correspond to certain desired values at different speed stages. If the pressure differential deviates to too large an extent, the deviation is recognized as a drift of the pressure sensor, and a correction value is determined in dependence on the drift, the subsequently measured pressure values being corrected with the aid of this correction value. In this manner it is possible to carry out a drift correction on the sensor with the pump arranged in the heart and even with the pump in operation.

4 Claims, 5 Drawing Sheets

FIG. 2
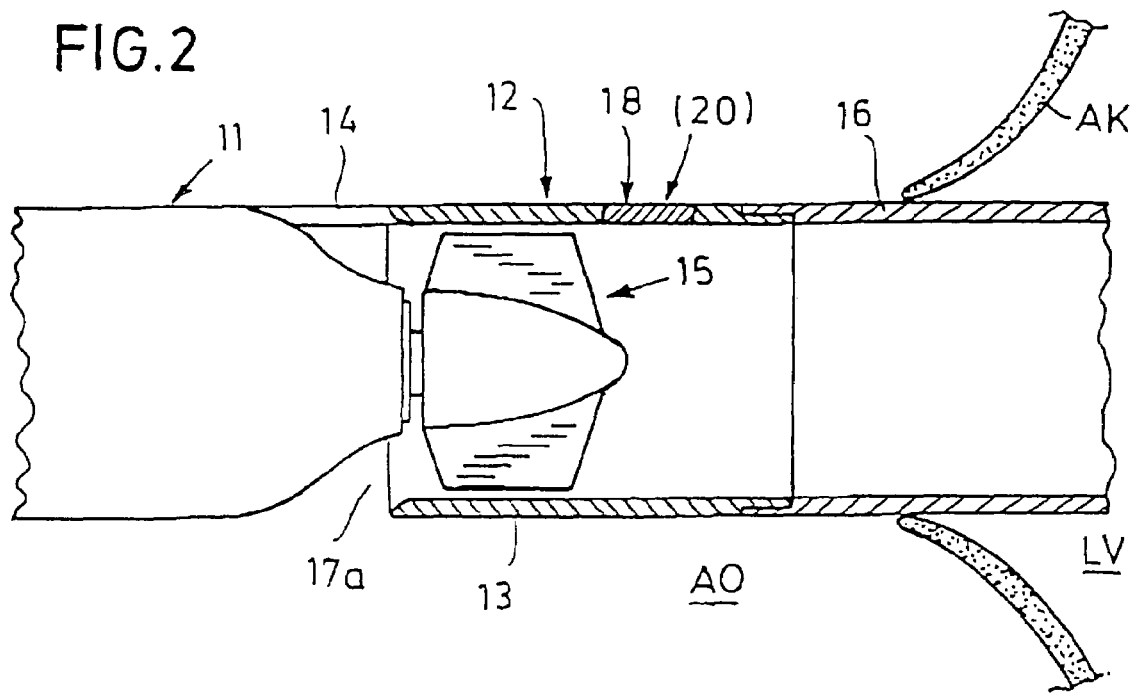
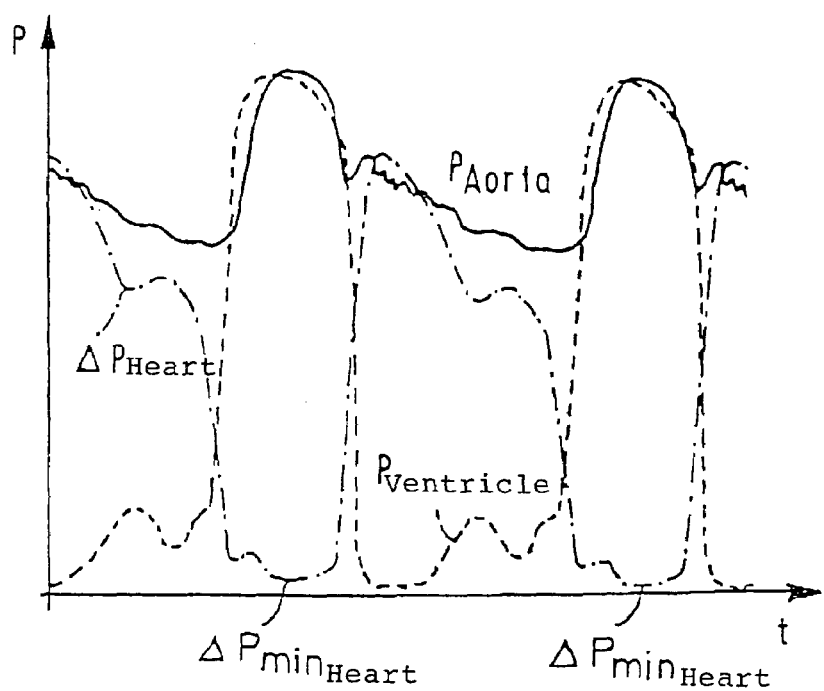
FIG. 3

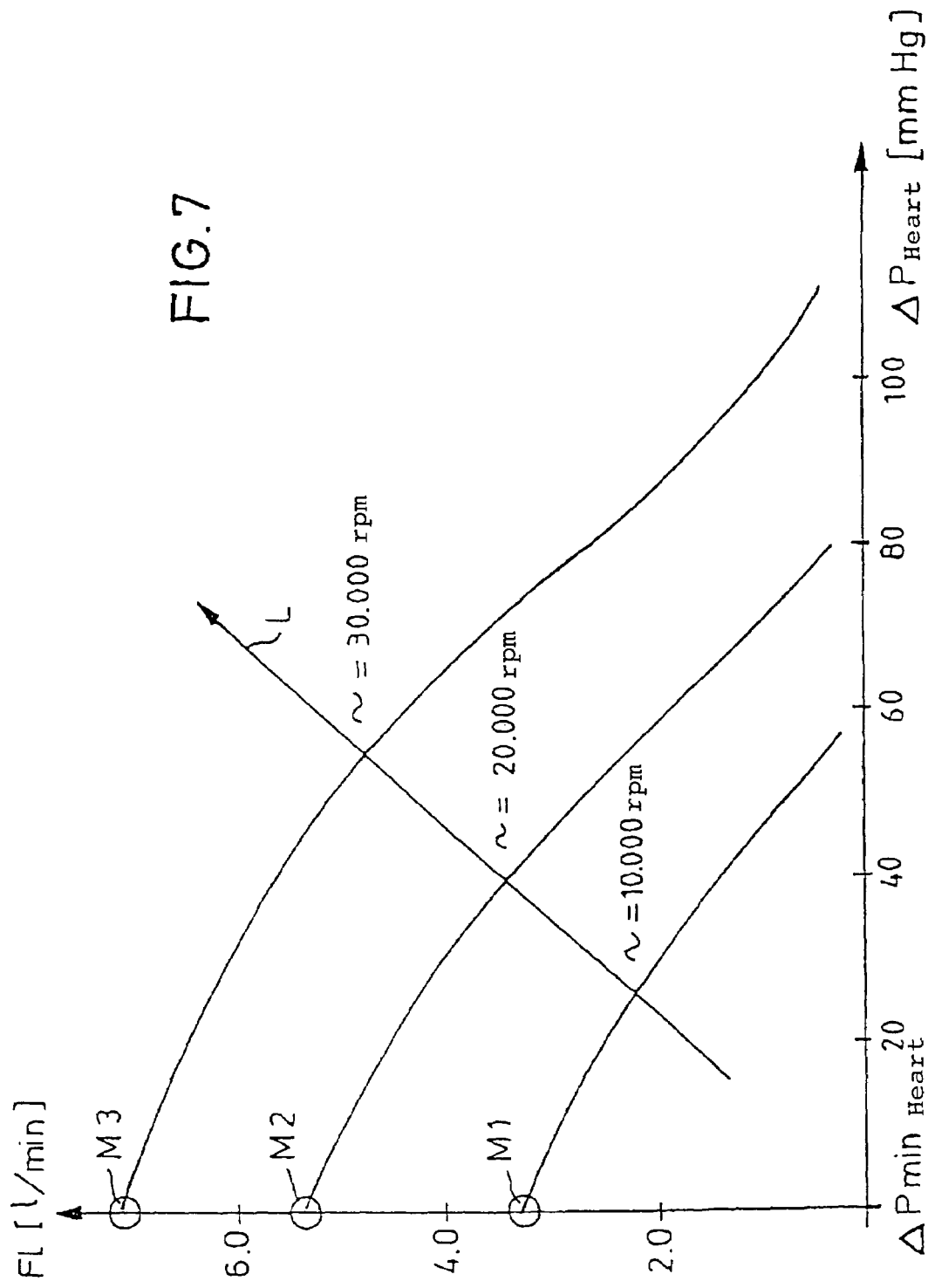

METHOD FOR CALIBRATING A PRESSURE SENSOR OR A FLOW SENSOR AT A ROTARY PUMP

BACKGROUND OF THE INVENTION

The invention relates to a method for calibrating a pressure sensor or a flow sensor at a rotary pump supporting the pulsating heart.

It is common practice to use an intracardiac rotary pump for supporting the heart activity. WO 98/43688 describes an intracardiac blood pump where the control of the pumping operation is carried out as a function of the measuring signal supplied by a pressure measuring means. On the basis of the measured pressure value the delivery rate of the pump can be determined. The pump casing made from a tube comprises in one case a pressure differential sensor which determines the pressure differential between the outlet pressure and the inlet pressure of the pump. The pump inlet is provided with a cannula which extends through the aortic valve in the case of a left-ventricular pump. This cannula causes additional losses which are, to a large extent, proportional to the pump speed and whose effects can be mathematically taken into account. An essential error source is the occurrence of a drift at the pressure sensor. Such a drift requires recalibration of the pressure sensor and/or determination of a correction value.

SUMMARY OF THE INVENTION

It is an object of the invention to suggest a method for calibrating a pressure sensor at a rotary pump supporting the pulsating heart, which method can be carried out in situ on the pump located in the heart such that it is not necessary to remove said pump.

The method according to the invention is in particular suitable for a pump implanted for a longer period (weeks or months). The calibration method is also applicable to implantable pumps as described in WO 97/49439. These are pumps supporting the heart activity which are placed around the heart and connected to the heart and the discharging vessels by means of inlet and outlet ducts. Such pumps are also referred to as paracardiac pumps.

The invention is based on the idea that in a blood pump which either extends through a cardiac valve or whose inlet cannula is separated from the outlet cannula by a natural cardiac valve, the pressure difference generally approaches zero when the cardiac valve is open. However, when the pump is provided with a cannula, no pressure difference of zero is reached when the pump is in operation, because a pressure drop occurs within the cannula which is due to inlet losses, frictional losses in the tube and a dynamic pressure reduction. Yet the time curve of the pressure progression shows a minimum when the cardiac valve is open. According to the invention, a table or curve of the desired pressure minimum values as a function of the pump speed is made up for an ideal drift-free pressure sensor. During pump operation the actual pressure minimum value of the pressure measurement taken by the pressure sensor is determined and said minimum value is compared with the desired pressure minimum value associated with the respective speed. From the difference between the pressure minimum values a correction value for the subsequently measured pressure values is determined. In this manner, a drift of the pressure sensor can be corrected with the rotary pump in operation.

The method according to the invention is preferably carried out with a pressure differential sensor, but it is also suitable for drift correction on absolute-pressure sensors.

The invention further relates to a method for calibrating a pressure differential sensor of a right-ventricular intracardiac pump. In this case the pressure differential is measured when the pump is out of operation. If the pressure differential exceeds a limiting value of e. g. 5 mmHg, a corresponding correction value is generated. This method, too, allows calibration without the pump having to be removed from the heart.

Another object of the invention is to suggest a method for calibrating a flow sensor at a rotary pump supporting the pulsating heart, which method can be carried out in situ on the pump located in the heart such that it is not necessary to remove the pump.

In the calibration method to be applied to the flow sensor the condition of the open cardiac valve is evaluated, in which the pressure difference over the cardiac value equals zero or is almost zero. The flow obtained then is entered in a table or curve as a function of the pump speed with the flow sensor in good working order. The respective speed is the flow maximum value. For recalibrating the flow sensor the actual flow maximum value of the flow measurement taken by the flow sensor is determined. On the basis of the difference between the actual flow maximum value and the desired flow maximum value corresponding to the same speed a correction value for the subsequently measured flow values is determined. In this manner, a drift of the flow sensor can be corrected with the rotary pump in operation. This method, too, is in particular suitable for pumps implanted for a longer period.

The invention further relates to a method for calibrating a flow sensor of an right-ventricular intracaridac pump. In this case the flow is measured with the pump out of operation. If the flow value exceeds a limiting value, a corresponding correction value is generated.

Hereunder embodiments of the invention are explained in detail with reference to the drawings in which:

BRIEF DESCRIPTION OF THE DRAWINGS

FIG. 2 shows an enlarged longitudinal section of the pumping portion of the pump, FIG. 3 shows a graphical representation of the variation with time of various pressures relative to the left ventrical, FIG. 7 shows a graphical representation of the dependence of the flow FL on the pressure differential $\Delta P_{heart}$, wherein the flow maximum values lie on the ordinate at $\Delta P_{minheart}=0$.

DETAILED DESCRIPTION OF PREFERRED EMBODIMENTS

Figure 1:
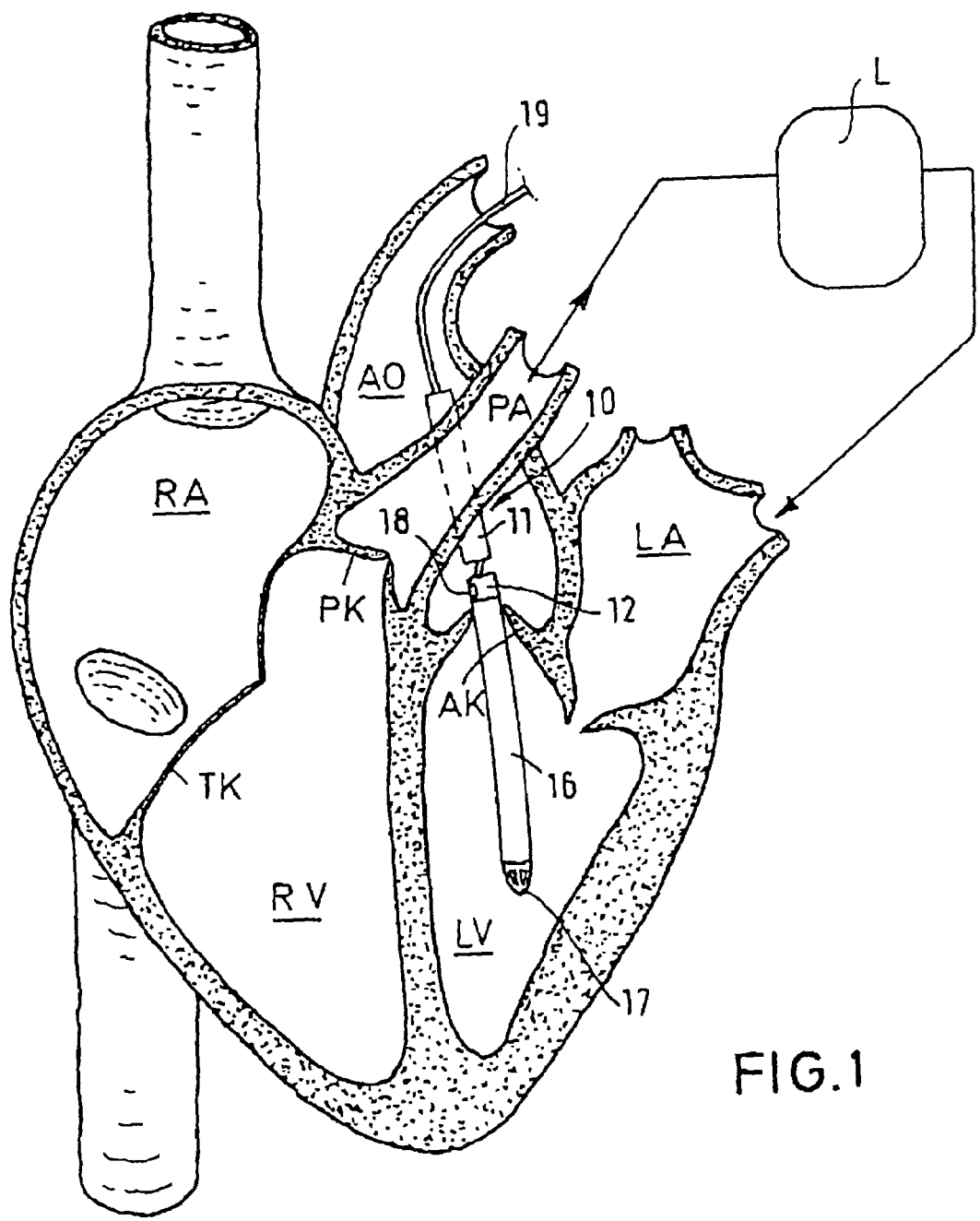
FIG. 1 shows a schematic representation of a left-ventricular pump located in the heart.

FIG. 1 shows a left-ventrical pump 10 supplying blood from the left ventrical LV to the aorta AO thus supporting the natural pulsating pumping action of the heart. The pump 10 extends through the aortic valve AK without affecting the latter's function.

FIG. 1 further shows the right atrium RA, the tricuspid valve TK and the right ventrical RV of the heart, as well as the pulmonary valve PK, the pulmonary artery PA leading to the lung L and the right atrium LA.

The pump 10 is a rotary pump as generally described in WO 98/43688. The pump comprises a driving portion 11 containing an electromotor and a pumping portion 12. According to FIG. 2 the pumping portion 12 comprises a tubular pump casing 13 which is connected via webs 14 with the driving portion 11. In the pump casing 13 an impeller 15 rotates which is connected with the motor shaft. Adjacent to the pump casing 13 a hose-shaped flexible cannula 16 is arranged which is provided with inlet openings 17 at its front end (FIG. 1). The outlet opening 17a of the pump is located in the transition area between the driving portion 11 and the pump casing 13.

On the pump casing 13 a pressure sensor 18 is provided which is configured here as a pressure differential sensor and measures the pressure differential between the internal pressure and the external pressure of the casing 13. The pressure sensor 18 is connected via lines (not shown), which extend through a catheter 19, with an extracorporeal measuring means. The catheter 19 adjoins the proximal end of the driving portion 11. Through the driving portion extend the supply lines for the electromotor. An external controller controls the operating speed of the electromotor and thus determines one of a plurality of speed stages at which the pump is operated.

The electromotor located in the driving portion 11 is operated as a function of the speed. The pressure difference, in combination with the speed, gives information about the volumetric flow of the pump.

The pressure sensor 18 comprises a membrane which is deformed due to the pressures applied to the two membrane faces. The pressure applied to the outside corresponds to the pressure of the surrounding vessel (aorta). The pressure within the pump casing corresponds to the pressure at the cannula tip minus the pressure loss of the cannula and the dynamic pressure reduction induced by the flow velocity. When the pump is arranged as shown in FIG. 1, the pressure differential measured by the pressure sensor 18 is as follows:

$$\Delta P = P_{aorta} - P_{ventricle} + P_{cannula}.$$

The variation with time of the two pressures $P_{aorta}$ and $P_{ventricle}$ is shown in FIG. 3. The pressure differential $\Delta P_{heart}$ is also shown. Every time the aortic valve AK is open, the pressure differential $\Delta P_{heart}$ is almost zero. This condition is designated $\Delta P_{minheart}$.

Figure 4:
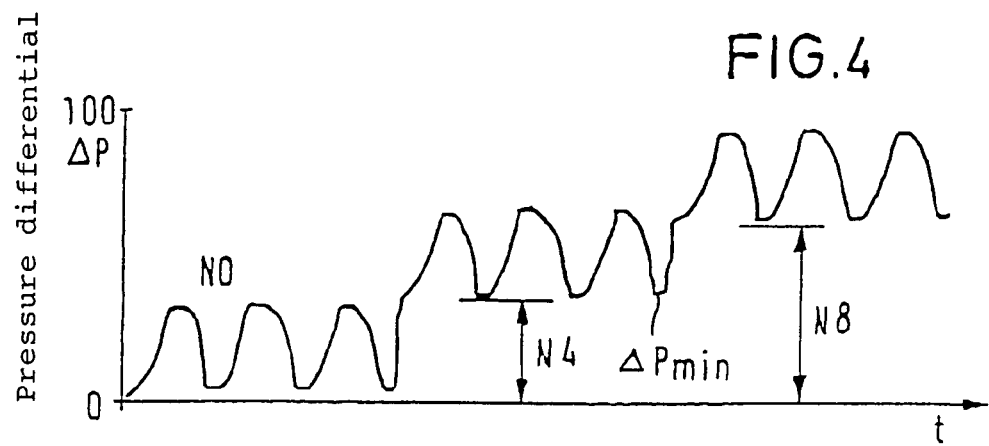
FIG. 4 shows the variation with time of the pressure differential at different speed or capacity stages of the left-ventrical pump.

FIG. 4 shows the variation with time of the pressure differential $\Delta P$ at various speed stages N0, N4 and N8 of the rotary pump. In the speed stage N0 the rotary pump is cut off. The pressure amplitude between systole and diastole produced by the natural heart activity is maintained to a large extent even during pump operation. However, according to the adjusted speed stage of the pump the general pressure level varies. The pressure differential minimum value $\Delta P_{min}$ is increased by exactly that value which arises due to the pumping support. If the tip of the cannula 16 is located in the left ventricle LV and the pump casing 13 in the aorta AO, the pressure difference $\Delta P$ is represented as a sinusoidal signal.

Figure 5:
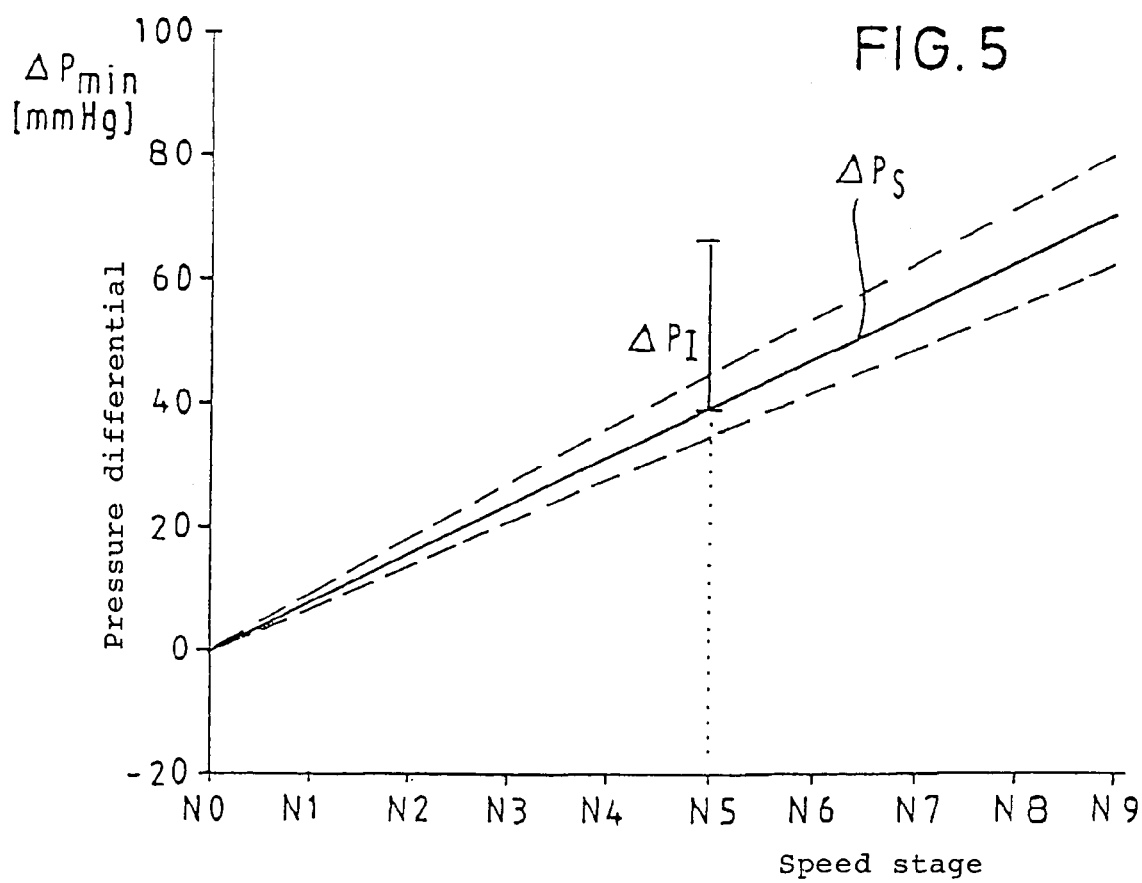
FIG. 5 shows a graphical representation of the minimum value of the differential pressure measured at the pressure difference as a function of the speed or capacity stage.

FIG. 5 shows the amount of the pressure differential minimum values $\Delta P_{min}$ as a function of the speed stage N0 to N9. It can be seen that the amount of the pressure differential minimum value increases proportionally to the speed. The curve $\Delta P_s$ shows the desired pressure minimum values. Around this curve a tolerance range is shown. If an actual pressure minimum value $\Delta P_I$ measured in a certain speed range, e. g. at speed N5, lies outside the tolerance range, the difference is formed by the acutal-pressure minimum value $\Delta P_I$ and the desired pressure minimum value $\Delta P_s$ at the same speed (here: N5). This difference forms the experienced drift of the pressure sensor. The drift is used for correction of the subsequently measured pressure values.

Figure 6:
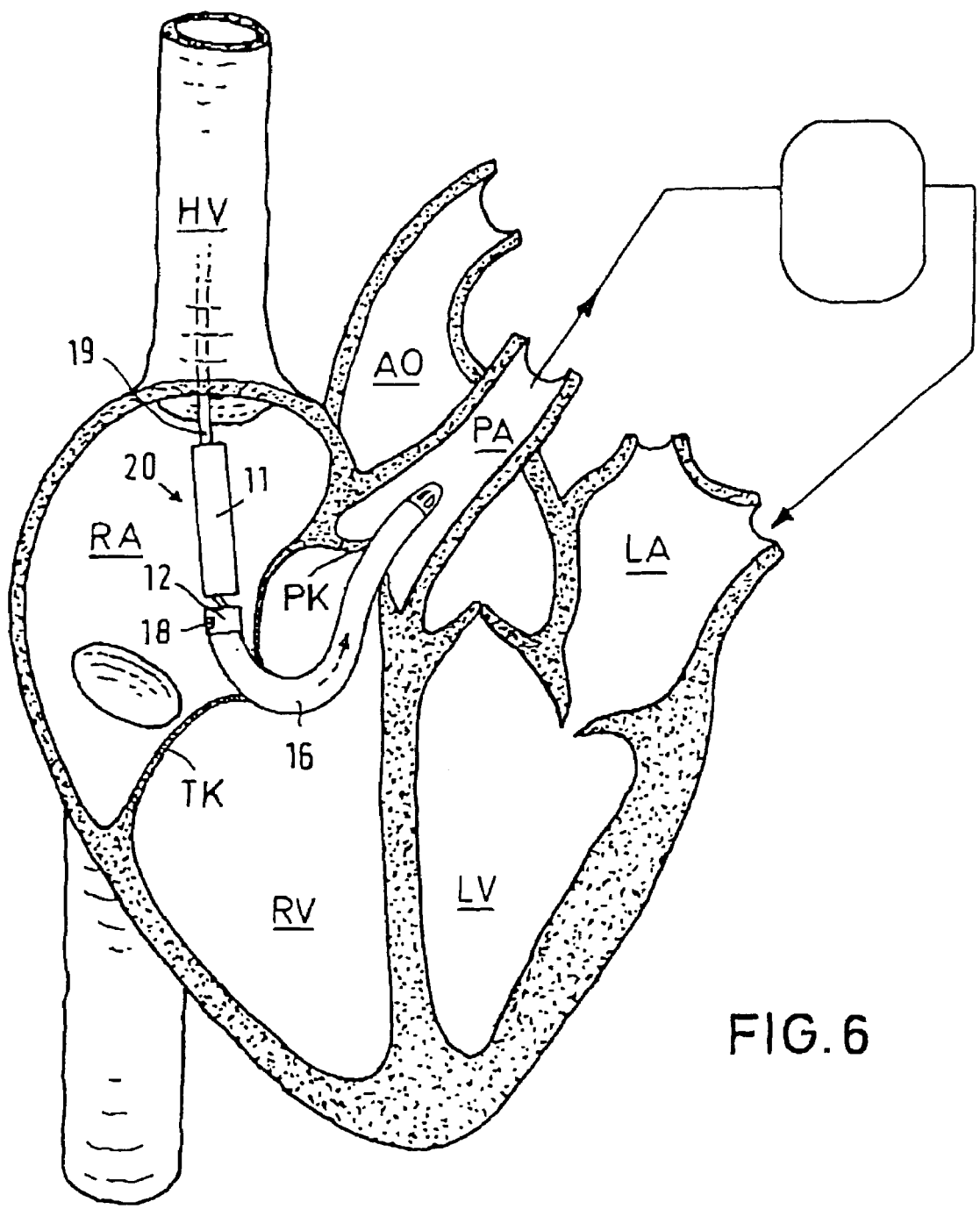
FIG. 6 shows a schematic representation of the heart containing a right-ventrical pump.

FIG. 6 shows an intracardiac right-ventrical pump which is generally configured in the same way as the pump 10 but supplies blood in reverse direction. The pump 20 is laid, together with the catheter 19, through the upper vena cava HV and is located in the right atrium RA, wherein the cannula 16 supplies blood through the tricuspid valve TK and the pulmonary valve PK into the pulmonary artery PA.

For calibrating the pressure sensor 18 of the right-ventrical pump 20 the pump 20 is placed out of operation and the pressure differential is measured. The pressure differential must amount on an average to 5 mmHg. If the pressure differential deviates from this value, a correction value for the pressure differentials subsequently measured with the pump in operation is determined on the basis of the deviation. In this manner, the drift of the pressure differential sensor is eliminated and a zero balance carried out.

Hereunder the flow measurement with the aid of a flow sensor is described. For this purpose it is assumed that the sensor shown in FIG. 2 is a flow sensor 20. This flow sensor is e. g. a hot-film anemometer or an ultrasonic Doppler sensor. The sensor primarily measures the velocity of the blood flow and thus the flow in the pump casing 13 which has a defined cross-section.

FIG. 7 shows the dependence of the flow FL on the pressure differential $\Delta P_{heart}$ at various pump speeds n. These speeds are plotted on line L. According to FIG. 7 each flow curve reaches it maximum at that location at which $\Delta P_{heart}$ equals zero or the curve has reached the minimum $\Delta P_{minheart}$. The maximum values are designated M1, M2, M3 in FIG. 7. Thus, when the aortic valve AK is open, a flow of M1 occurs at a speed of 10000 rpm, a flow of M2 occurs at a speed of 20000 rpm and a flow of M3 occurs at a speed of 30000 rpm. These flow maximum values M1, M2, M3 for the various speeds are stored in a table or a curve and thus represent the desired flow maximum values. For recalibration of the flow sensor the actual maximum value of the flow is determined at a random speed of the pump, and from the difference to the desired maximum value a correction value for drift compensation is determined.

In the right-ventricle pump shown in FIG. 6 it is also possible to use a flow sensor 20 instead of the pressure sensor 18. In this case the flow is measured with the pump out of operation. If the indication shows a non-zero flow, this flow value is used as a correction value for drift correction.

What is claimed is:
1. Method for calibrating an in vivo pressure sensor at a rotary pump supporting a pulsating heart, the method comprising the following steps:
making up a table or a curve of desired pressure minimum values ($\Delta P_S$) as a function of pump speed (n) for a pressure sensor in good working order,
determining an actual pressure minimum value ($\Delta P_I$) of the pressure measured by said pressure sensor at said rotary pump supporting a pulsating heart at a first speed, determining the difference between such actual pressure minimum value ($\Delta P_I$) and the desired pressure minimum value ($\Delta P_S$) at said first speed, and determining a correction value for correcting a subsequently measured pressure value by said in vivo pressure sensor at a second speed on the basis of the determined difference.

2. Method according to claim 1, wherein the in vivo pressure sensor is a pressure differential sensor which measures a pressure differential between the outside and the inside of a tubular pump casing.

3. Method according to claim 1, wherein said pump comprises an intracardiac left-ventricular pump.

4. Method according to claim 1, wherein said pump comprises a paracardiac heart pump.

* * * * *